US008102259B2

(12) United States Patent
Merritt

(10) Patent No.: US 8,102,259 B2
(45) Date of Patent: Jan. 24, 2012

(54) FLUORESCENT LIGHT IMMUNITY THROUGH SYNCHRONOUS SAMPLING

(75) Inventor: David E. Merritt, Rocklin, CA (US)

(73) Assignee: Honeywell International Inc., Morristown, NJ (US)

( * ) Notice: Subject to any disclaimer, the term of this patent is extended or adjusted under 35 U.S.C. 154(b) by 1499 days.

(21) Appl. No.: 11/581,830

(22) Filed: Oct. 17, 2006

(65) Prior Publication Data

US 2008/0088432 A1 Apr. 17, 2008

(51) Int. Cl.
*G08B 13/00* (2006.01)
*A61B 5/00* (2006.01)

(52) U.S. Cl. ........................................ 340/541; 600/336

(58) Field of Classification Search .................. 340/541, 340/552, 426, 554, 553, 425.5, 545.2, 545.3; 364/572; 600/336
See application file for complete search history.

(56) References Cited

U.S. PATENT DOCUMENTS 4,054,871 A * 10/1977 Terrell et al. .................... 342/28
4,220,412 A * 9/1980 Shroyer et al. ................ 356/218
4,322,722 A * 3/1982 Kozdon ........................ 340/554
4,625,199 A 11/1986 Pantus
4,908,600 A 3/1990 Martinez
5,576,977 A * 11/1996 Eskildsen ..................... 702/190
5,581,237 A * 12/1996 DiPoala ........................ 340/554
5,684,458 A 11/1997 Calvarese
6,509,835 B1 1/2003 Krubiner et al.
6,677,887 B2 * 1/2004 Harman .......................... 342/28
6,756,936 B1 * 6/2004 Wu ............................... 342/175
7,190,985 B2 * 3/2007 Petersen et al. ............... 600/336
2002/0175815 A1 11/2002 Baldwin
2006/0139164 A1 * 6/2006 Tsuji ............................. 340/522

FOREIGN PATENT DOCUMENTS

FR 2 460 012 1/1981
WO WO 00/52656 9/2000
WO WO 02/063771 A2 8/2002

* cited by examiner

*Primary Examiner* — Benjamin C Lee
*Assistant Examiner* — Sigmund Tang
(74) *Attorney, Agent, or Firm* — Husch Blackwell

(57) ABSTRACT

A system and method for reducing interference caused by fluorescent light on alarm system components using synchronous sampling is provided. The system incorporates a detector for detecting the line frequency of a power line and synchronizes the security system to the detected line frequency. The detector employed may be a light emitting diode configured as a photodetector, an antenna tuned for frequencies near 55 Hz, or a filter connected to an output of a Microwave channel.

18 Claims, 6 Drawing Sheets

FLUORESCENT LIGHT IMMUNITY THROUGH SYNCHRONOUS SAMPLING

FIELD OF THE INVENTION

The present invention relates generally to security systems. More specifically, the present invention relates to a system and method for fluorescent light immunity of security system sensors through synchronous sampling of electrical line frequency.

BACKGROUND OF THE DISCLOSURE

Microwave Doppler transceivers are devices that transmit a Microwave pulse at a frequency in the GHz region of the electromagnetic spectrum, and receive return pulses that are reflect by objects. Stationary objects reflect a return pulse at a frequency equal to the transmitted frequency. On the other hand, an object that is in motion, towards or away, from the Microwave Doppler transceivers will shift the original frequency and reflect a return signal at a frequency that is offset by a particular frequency, based on the speed and direction of the object relative to the microwave Doppler source. This phenomenon is known as a Doppler shift.

Security systems utilize this Doppler shift to detect motion, which may indicate an unauthorized intrusion into the monitored area. However, Microwave Doppler transceivers are sensitive to fluorescent lights, which can cause false alarms and mask legitimate signals. Traditional filtering techniques using passbands in the range of 5 Hz to 500 Hz, are impractical because the noise falls within the passband frequency range. Anti-masking systems are equally sensitive to noise emanating from fluorescent lights, as well.

Fluorescent lights operate by supplying a high voltage pulse across a space filled with a gas that, once excited by the pulse, causes phosphor particles to fluoresce, thus emitting light. This process charges and discharges the gas, causing the gas particles to move back and forth. The Microwave Doppler transceiver readily detects the motion of the gas particles and interprets it as an intruder, resulting in a false alarm.

Solutions, such as hardware notch filters, are impractical for high volume low cost manufacturing and in addition, may remove too much of the desired signal. Presently, Microwave Doppler transceivers are designed to reject line noise by sampling at 50 Hz, creating a comb filter tuned to multiples of the sampling frequency.

In the U.S., and other regions of the world, the line frequency is set to 60 Hz, requiring a different sampling rate. Products designed for use in both 50 Hz countries and 60 Hz countries overcome this problem by including a DIP switch that the installer is required to set based on the local line frequency, thus allowing a single product to be sold in all regions. However, DIP switches are undesirable to customers, as they require time to set and introduce the potential for errors resulting from an incorrectly set DIP switch.

In some areas of the world frequency control of the 50 or 60 Hz line frequency may be imprecise. If the line frequency were not exactly 50 Hz, the 50 Hz sampling would introduce a low frequency alias that could be strong enough to produce a false signal. For example if the line were at 51 Hz, a 1 Hz alias would result that would not be completely attenuated from the 5 Hz analog high pass filter. A better solution would be to sample exactly at the line frequency, whatever that happened to be. In these cases, a DIP switch allowing selection of one of a predefined set of line frequencies is entirely inadequate

SUMMARY OF THE DISCLOSURE

The present invention provides a system and method of automatically detecting and synchronizing to the line frequency based on detected ambient signals. Consequently, installer intervention is eliminated while also correcting for countries that are "approximately 50 Hz".

The present invention for providing fluorescent light immunity for intrusion detection systems executes the steps of detecting ambient electromagnet (EM) signals; amplifying the ambient EM signals; filtering the ambient EM signals to isolate frequencies indicative of noise resulting from a frequency of an electrical line; and synchronizing the intrusion detection system to interrogate a monitored area at time intervals corresponding to the isolated frequencies.

An embodiment of the present invention for providing fluorescent light immunity for intrusion detection systems includes a signal indicative of fluorescent light flicker, which may be received or detected by a light emitting diode adapted as a photodetector, a tuned antenna, or a capacitively coupled alarm loop. An amplifier increases the gain of the signal. A filter isolates a frequency, from the amplified signal, corresponding to second harmonics of a line frequency of an alternating current (AC) power line. A squaring amplifier generates a square-wave signal derived from the filtered signal. A controller synchronizes the intrusion detection system to interrogate a monitored area at time intervals corresponding to the square-wave signal.

Alternatively, an embodiment of the present invention for providing fluorescent light immunity for intrusion detection systems may include a microwave transceiver adapted for motion detection. The microwave transceiver generates an electromagnetic (EM) signal in the microwave range. An amplifier increases the gain of a portion of the EM signal, which has been diverted to the amplifier. A filter isolates a frequency corresponding to second harmonics of a line frequency of an alternating current (AC) power line. A squaring amplifier generates a square-wave signal derived from the filtered signal. A controller synchronizes the intrusion detection system to interrogate a monitored area at time intervals corresponding to the square-wave signal.

BRIEF DESCRIPTION OF THE DRAWINGS

These and other features, aspects, and advantages of the present invention will become better understood with regard to the following description, appended claims, and accompanying drawings wherein:

DETAILED DESCRIPTION OF DISCLOSURE

Figure 1:
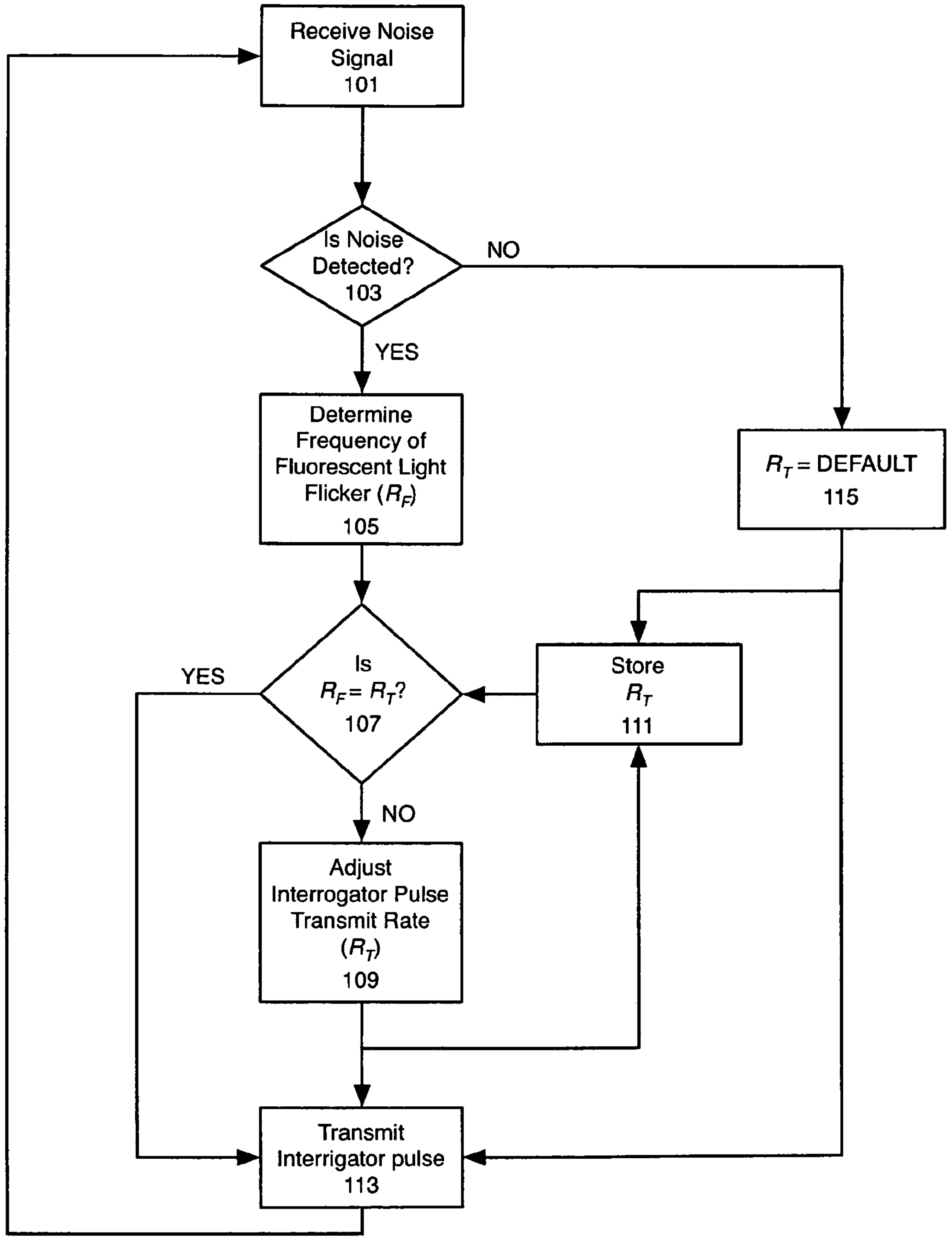
FIG. 1 illustrates a flow diagram of the process for performing an embodiment of the present invention.

A method for implementing an embodiment of the present invention, as shown in FIG. 1, begins with a noise signal being received by a detecting means in step 101. The received noise signal may be amplified and filtered to isolate the noise in step 101 as well. The noise signal is subsequently analyzed in step 103 to determine if noise is present at levels above a predefined threshold.

In the case where noise is detected, the frequency of the noise is determined in step 105. This noise frequency is directly representative of fluorescent light flicker frequency ($R_F$). The flicker frequency ($R_F$) is compared in step 107 to a transmit rate ($R_T$) stored in a memory means. The transmit rate ($R_T$) is a rate, or frequency, at which an interrogator pulse is emitted by a transceiver means. The transceiver means may be a Microwave transceiver or other such detection device that may be affected by fluorescent light. If the flicker frequency ($R_F$) is equal to the stored transmit rate ($R_T$), the process advances to step 113, where the transceiver means is directed to transmit an interrogator pulse at the stored transmit rate ($R_T$).

However, in the event that the flicker frequency ($R_F$) does not equal the stored transmit rate ($R_T$), the transmit rate ($R_T$) is synchronized to the flicker frequency ($R_F$) in step 109 and the new transmit rate ($R_T$) is stored in a memory means in step 111. Subsequently, the process continues to step 113, where the transceiver means is directed to transmit an interrogator pulse at the newly synchronized transmit rate ($R_T$).

Referring back to step 103, in the case where no noise is detected above the predefined threshold, the process advances from step 103 to step 115, where a default transmit rate ($R_T$) is set and stored in the memory means. Subsequently, in step 113 the transceiver means is directed to transmit an interrogator pulse at the default transmit rate ($R_T$), which may be a rate of 50 HZ, 60 Hz, or any other appropriate frequency. The interrogator pulse interrogates, or scans, the monitored area for indications of an intrusion.

This process may be configured to continuously monitor the ambient noise conditions of the environment in which the detector is situated. In this way, when changes occur, such as a fluorescent light being turned on or off, the transceiver can be properly adjusted to compensate for the noise.

Figure 2:
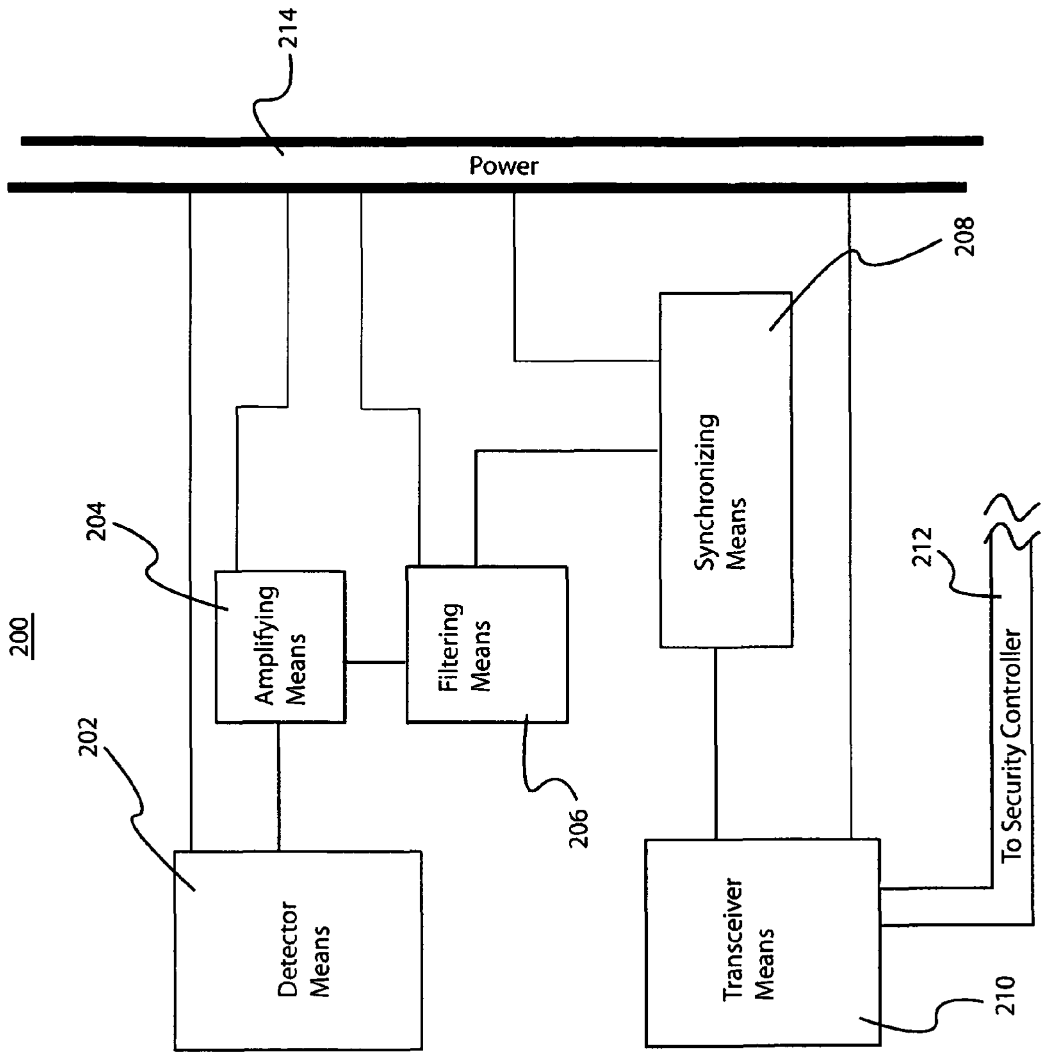
FIG. 2 illustrates a block representation of an embodiment of the present invention.

Referring to FIG. 2, a block representation of an embodiment of the present invention is shown. The present embodiment provides a detector means 202, which may be a light emitting diode adapted as a photodetector, a tuned antenna, or a capacitively coupled alarm loop. A noise signal received by the detector means 202 is provided to an amplifier means 204, where the noise signal is amplified to a sufficient level for further processing. The amplified signal is relayed to a filtering means 206, where the noise signal indicative of fluorescent light flicker is filtered from any other background noise that may be present in the noise signal.

A synchronization means 208, receives the filtered signal from the filtering means 206. The synchronization means 208 determines the frequency of the filtered signal, thus determining the flicker rate of the fluorescent light, and adjusts the transmission timing of the transceiver 210 to match the flicker rate.

The transceiver means 210 transmits an interrogator signal at a microwave frequency in sync with the flicker of the fluorescent light. There are several microwave frequencies including approximately 24 GHz, 10.2 GHZ, and 2.4 GHZ that may be utilized as an interrogator signal. In this way, the return signal reflected by the gas of the fluorescent light will not register as an intrusion, because the intrusion detector 200 would not detect any relative motion.

In addition, the intrusion detector 200 is powered by DC or AC voltage transmitted over wiring 214 running between the intrusion detector 200 and a security system controller (not shown), or DC voltage produced from an internally housed battery or other power generation device, such as a solar cell. A data line 212 is provided as well, connecting the intrusion detector 200 with the security system controller. While the data line 212 may be provided as wiring, alternatively the data line 212 may be a wireless transmission unit.

Figure 3:
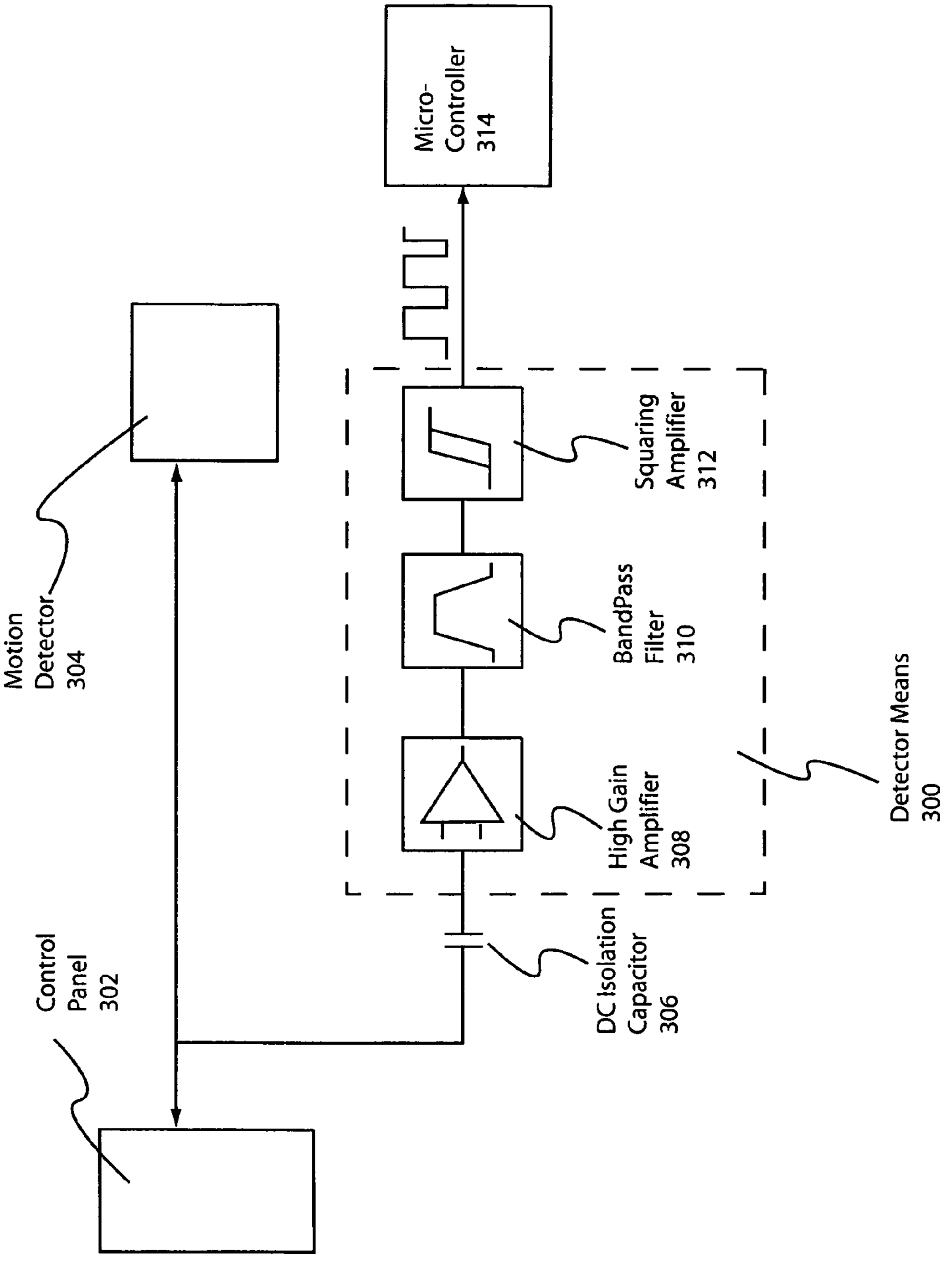
FIG. 3 illustrates a schematic representation of an embodiment of the present invention having an amplifier capacitively coupled to an alarm loop.

In an embodiment of the present invention, as shown in FIG. 3, the detection system 300 includes a high gain amplifier 308, a bandpass filter 310, and a squaring amplifier 312. Additionally, a capacitor 306 is disposed between the high gain amplifier 308 and the alarm system wiring running between the alarm system control panel 302 and a motion detector 304. The capacitor provides direct current (DC) isolation between the detector system 300 and the alarm system wiring, thus allowing only alternating current (AC) to pass to the high gain amplifier 308. The system wiring may be either an alarm loop used for communicating signals between the motion detector and the control panel, or a power line used to energize the alarm system.

The high gain amplifier 308 amplifies the AC signal and relays the amplified signal to the bandpass filter 310. The bandpass filter 310 is adapted to filter either the 100 Hz or 120 Hz second harmonics from the amplified signal. However, a preferred bandpass filter would have a center frequency of 110 Hz, thus allowing the bandpass filter to filter both 100 Hz and 120 Hz second harmonics adequately. Other center frequencies may be used, as well, depending on the specific situation.

The filtered second harmonics are passed to a squaring amplifier 312, which receives the sinusoidal waveform of the second harmonics and outputs a corresponding square-wave signal. The output square-wave signal is provided to a micro-controller 314 as a control signal input used to provide the synchronization timing for a motion detection system. This apparatus would essentially provide a 5' antenna at a minimum—longer in most cases—having a 1K minimum impedance to ground. However, switching noise and test signals originating from the security system control panel must be regulated to reduce interference.

Figure 4:
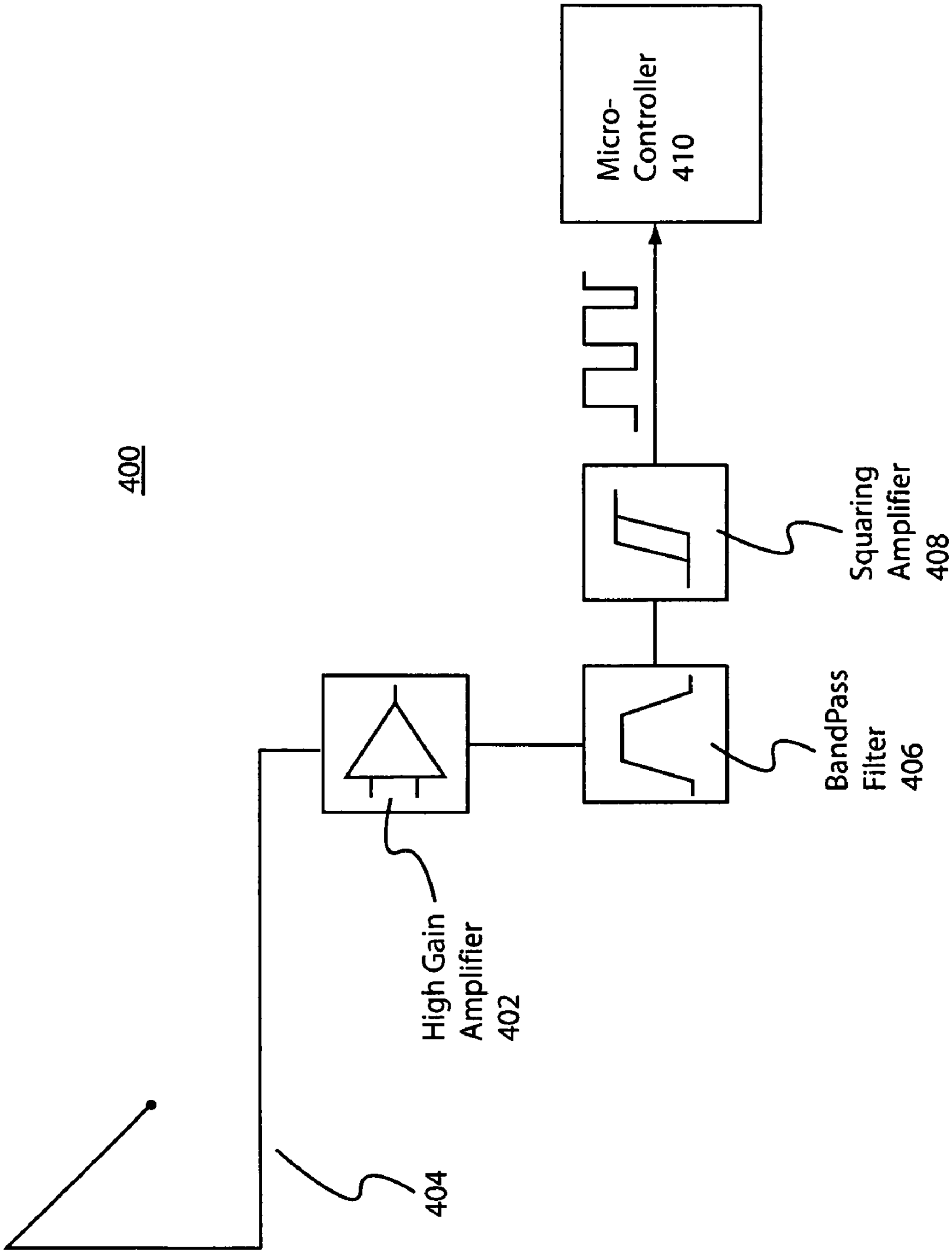
FIG. 4 illustrates a schematic representation of an embodiment of the present invention having a tuned antenna.

Alternatively, in FIG. 4, a detector system is formed from an amplifier 402, a wire-track antenna 404, a bandpass filter 406 and a squaring amplifier 408. The amplifier 402 is coupled to the wire-track antenna 404 formed on a circuit board. The wire-track antenna 404 may be an inch or more in length, as necessary, and adapted to receive signals in the 50 Hz to 60 Hz range. The wire-track antenna 404 receives electromagnetic noise, which is amplified by the amplifier 402. The bandpass filter 406 filters the amplified noise signal and the second harmonics of the noise signal are output to the squaring amplifier 408. The squaring amplifier 408 receives the sinusoidal waveform of the second harmonics and outputs a corresponding square-wave signal. The output square-wave signal is provided to a micro-controller 410 as a control signal input used to provide the synchronization timing for a motion detection system.

Since AC power lines emit electromagnetic noise into the surrounding environment at a frequency equal to the AC line frequency, detecting this electromagnetic line noise would allow a determination of the line frequency of the power being provided to fluorescent light fixtures. The AC line frequency, which in the U.S. is set to 60 Hz, is directly linked to the flicker rate of the fluorescent light.

Figure 5:
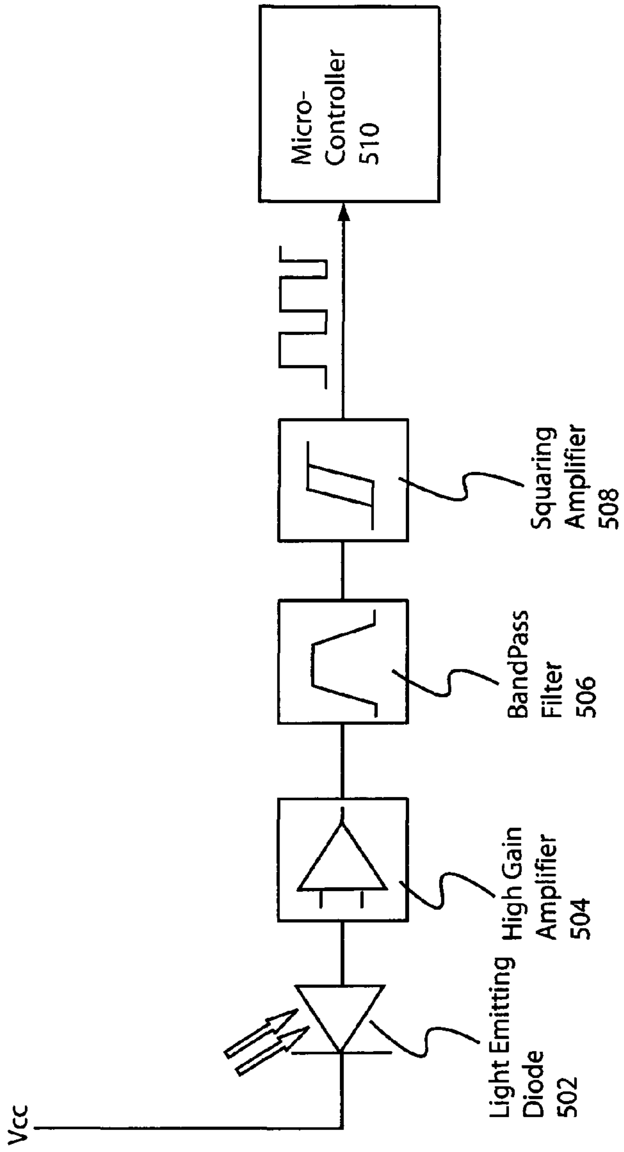
FIG. 5 illustrates a schematic representation of an embodiment of the present invention having an LED adapted as a photodetector.

Further, the flicker rate can be detected directly using a light emitting diode (LED) or photo diode, as shown in FIG. 5. LEDs exhibit a little known and rarely documented ability to act as photodetectors. This ability allows LEDs, which may already be present in an intrusion detector to be co-opted to serve as flicker rate detecting components. The benefit of directly detecting the flicker rate in this manner is that if none of the lights in the room are strong enough to generate a signal in the LED, then no Microwave jamming issue would be present either.

As shown in FIG. 5, another alternative detector system incorporates an LED or photo diode 502, a high gain amplifier 504, bandpass filter 506 and a squaring amplifier 508. The LED 502 is positioned such that ambient light readily impacts the LED 502, thus inducing a faint current flow. The high gain amplifier 504 amplifies the induced current, outputting an amplified signal. The high gain amplifier 504 may be either a voltage amplifier or a transconductance amplifier depending on the particular LED configuration used.

As in the previous embodiments of the detector means, the bandpass filter 506 filters the amplified noise signal and the second harmonics of the noise signal are output to the squaring amplifier 508. The squaring amplifier 508 receives the sinusoidal waveform of the second harmonics and outputs a corresponding square-wave signal. The output square-wave signal is provided to a micro-controller 510 as a control signal input used to provide the synchronization timing for a motion detection system.

Figure 6:
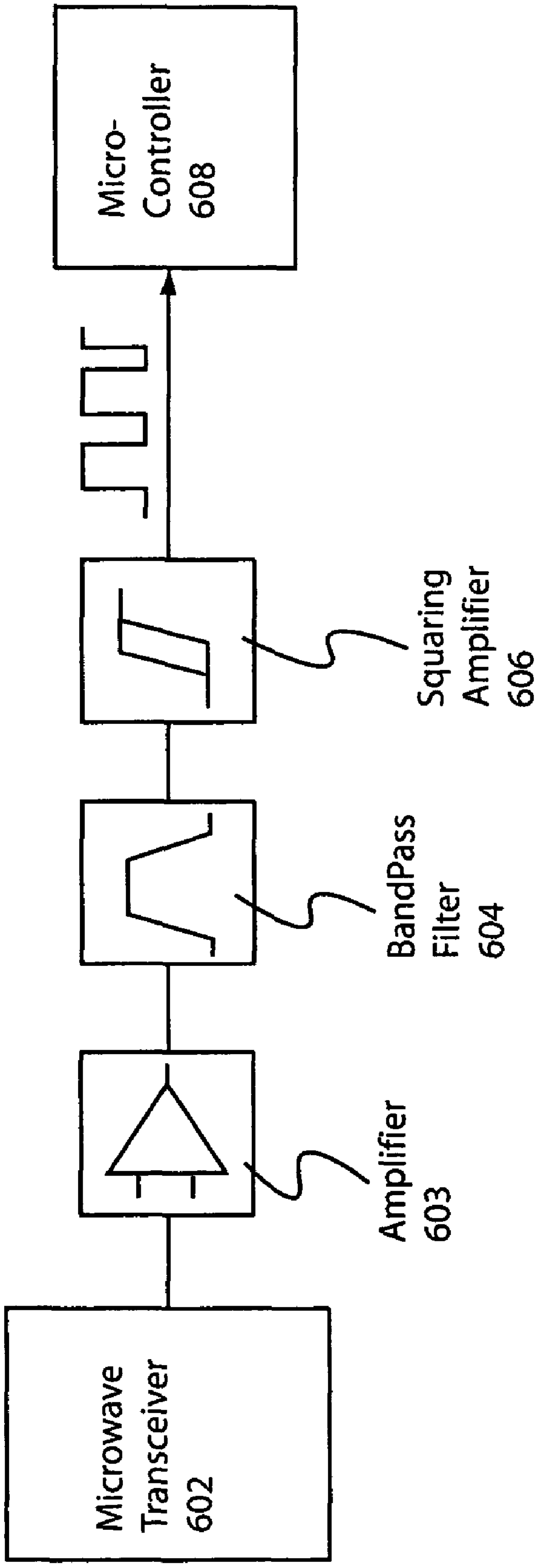
FIG. 6 illustrates a schematic representation of an embodiment of the present invention using an output from a Microwave channel of a Microwave Doppler transceiver.

Furthermore, FIG. 6 shows a further alternative embodiment of a detector system in which an output from a Microwave channel of a Microwave Doppler transceiver 602 is diverted and fed through an amplifier 603 for amplification followed by a bandpass filter 604, which filters either the 100 Hz or 120 Hz second harmonics. A squaring amplifier 606 squares the filtered second harmonics and a corresponding square-wave signal is output. The output square-wave signal is provided to a micro-controller 608 as a control signal input used to provide the synchronization timing for a motion detection system.

The advantage of using the noise off the Microwave channel is that if not enough noise is present to be detected, then there would not be enough noise to cause a problem for the intrusion detector. If this method were used, a soft synchronizing scheme would preferably be used, allowing the sample rate to be changed slowly. This is to prevent normal walking activities causing false triggering, because certain walking speeds will generate legitimate signals around 100 and 120 Hz.

Any of the above-described detector system may be incorporated into the assembly described in FIG. 2, replacing the detector means, amplifying means and filtering means. However, the described embodiments of the present invention are intended to be illustrative rather than restrictive, and are not intended to represent every embodiment of the present invention. Various modifications and variations can be made without departing from the spirit or scope of the invention as set forth in the following claims both literally and in equivalents recognized in law.

What is claimed is:

1. A system for providing fluorescent light immunity for an intrusion detection system comprising:

a transceiver that transmit microwave interrogator pulses at time intervals that correspond to a transmit rate and receive microwave pulses reflected from an intruder for intrusion detection;

means for detecting ambient electromagnetic (EM) signals from a fluorescent light;

means for amplifying said ambient EM signals;

means for filtering said ambient EM signals to isolate frequencies indicator of noise resulting from a frequency of an electrical line powering said fluorescent light; and means for synchronizing said intrusion detection system to interrogate a monitored area at times intervals corresponding to said isolated frequencies wherein the means for synchronizing adjusts the transmit rate to match the noise frequency of the electrical line.

2. The system as in claim 1, wherein said detecting means detects ambient EM signals present in an output of a Microwave source, said Microwave output being passed through a filter for isolating second harmonics.

3. The system as in claim 1, wherein said detecting means is coupled to an incoming power line by way of a capacitor, said capacitor preventing DC signals from propagating to said amplifying means and allowing AC signals to propagate to said amplifying means.

4. The system as in claim 1, wherein said detecting means is coupled to an alarm loop by way of a capacitor, said capacitor preventing DC signals from propagating to said amplifying means and allowing AC signals to propagate to said amplifying means.

5. The system as in claim 1, wherein said detecting means is an antenna tuned to a predefined center frequency lying in the frequency range associated with noise produced by said electrical line.

6. The system as in claim 5, wherein said frequency range being between 50 Hz and 60 Hz.

7. A method for providing fluorescent light immunity for an intrusion detection systems, said method comprising:

transmitting microwave interrogator pulses at time intervals that define a transmit frequency, and receiving microwave pulses reflected from an intruder for intrusion detection;

detecting ambient electromagnetic (EM) signals from a fluorescent light;

amplifying said ambient EM signals;

filtering said ambient EM signals to isolate frequencies indicative of noise resulting from a frequency of an electrical line powering said fluorescent light; and synchronizing said intrusion detection system to interrogate a monitored area at times intervals corresponding to said isolated frequencies by adjusting the transmit frequency to match the noise frequency of the electrical line.

8. The method as in claim 7, wherein said detecting detects ambient EM signals present in an output of a Microwave source, said Microwave output being passed through a filter for isolating second harmonics.

9. The method as in claim 7, wherein said detecting is performed via a capacitively coupled incoming power line.

10. The method as in claim 7, wherein said detecting is performed via a capacitively coupled alarm loop.

11. The method as in claim 7, wherein said detecting means is an antenna tuned to a predefined center frequency lying in the frequency range associated with noise produced by said electrical line.

12. The method as in claim 11, wherein said frequency range being between 50 Hz and 60 Hz.

13. A system for providing fluorescent light immunity for an intrusion detection systems, said fluorescent light immunity system comprising:

a transceiver that transmit microwave interrogator pulses at time intervals that correspond to a transmit rate and receives microwave pulses reflected from an intruder for intrusion detection;

an antenna for receiving an electromagnetic (EM) signal indicative of fluorescent light flicker to generate an EM output signal;

an amplifier for increasing the gain of said EM output signal;

a filter for isolating from the amplified EM output signal a frequency corresponding to second harmonics of a line frequency of an alternating current (AC) power line powering the fluorescent light;

a squaring amplifier for generating a square-wave signal derived from said filtered signal; and a controller for synchronizing said intrusion detection system to interrogate a monitored area at time intervals corresponding to said square-wave signal wherein the controller adjusts the transmit frequency of the transceiver to match the second harmonic of the line frequency of the alternative AC power line.

14. The system as in claim 13, wherein said signal is EM noise emitted by said AC power line.

15. The system as in claim 13, wherein said antenna is a wire-track antenna formed on a circuit board.

16. The system as in claim 13, wherein said antenna is formed by a portion of intrusion detection system wiring, said wiring being coupled to said amplifier by way of a capacitor, said capacitor preventing direct current (DC) signals from propagating to said amplifier and allowing AC signals to propagate to said amplifier.

17. The method as in claim 13, wherein said antenna is tuned to a frequency range between 50 Hz and 60 Hz.

18. A system for providing fluorescent light immunity for an intrusion detection systems, said fluorescent light immunity system comprising:

a microwave transceiver adapted for motion detection, said microwave transceiver generating pulses of an electromagnetic (EM) signal in the microwave range, the pulses emitted at time intervals that define a transmit frequency, and receiving pulses of said EM signal reflected from an intruder for intrusion detection;

an amplifier for increasing the gain of a portion of said the received EM signal, said portion having been diverted to said amplifier;

a filter for isolating a frequency corresponding to second harmonics of a line frequency of an alternating current (AC) power line powering a fluorescent light in the vicinity of the microwave transceiver;

a squaring amplifier for generating a square-wave signal derived from said filtered signal; and a controller for synchronizing said intrusion detection system to interrogate a monitored area at time intervals corresponding to said square-wave signal wherein the controller adjusts the transmit frequency of the generated pulses to match the second harmonic of the line frequency of the AC power line.

* * * * *